(12) United States Patent
Kudo et al.

(10) Patent No.: US 11,805,969 B2
(45) Date of Patent: Nov. 7, 2023

(54) BIOLOGICAL INFORMATION MEASURING APPARATUS, BIOLOGICAL INFORMATION MEASUREMENT METHOD, AND RECORDING MEDIUM

(71) Applicants: Kiwamu Kudo, Ishikawa (JP);
Yoshihiro Misaka, Ishikawa (JP);
Noriyuki Tomita, Ishikawa (JP);
Hirofumi Morise, Kanagawa (JP)

(72) Inventors: Kiwamu Kudo, Ishikawa (JP);
Yoshihiro Misaka, Ishikawa (JP);
Noriyuki Tomita, Ishikawa (JP);
Hirofumi Morise, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 617 days.

(21) Appl. No.: 16/832,077

(22) Filed: Mar. 27, 2020

(65) Prior Publication Data
US 2020/0305747 A1   Oct. 1, 2020

(30) Foreign Application Priority Data

Apr. 1, 2019   (JP) ................................. 2019-070167

(51) Int. Cl.
*A61B 5/245* (2021.01)
*A61B 5/06* (2006.01)
(Continued)

(52) U.S. Cl.
CPC ............ *A61B 5/245* (2021.01); *A61B 5/0033* (2013.01); *A61B 5/066* (2013.01); *A61B 5/369* (2021.01);
(Continued)

(58) Field of Classification Search
CPC ....... A61B 5/245; A61B 5/0033; A61B 5/066; A61B 5/369; A61B 5/746; A61B 5/242;
(Continued)

(56) References Cited

U.S. PATENT DOCUMENTS

| 6,370,414 | B1 | 4/2002 | Robinson |
| 2002/0115927 | A1* | 8/2002 | Tsukada ............... A61B 5/4064 600/409 |

(Continued)

FOREIGN PATENT DOCUMENTS

| JP | H04-109932 | 4/1992 |
| JP | H04-135536 | 5/1992 |

(Continued)

OTHER PUBLICATIONS

Schwartz et al., ("Registration of MEG/EEG Data with 3D MRI: Methodology and Precision Issues", Brain Topography, vol. 9; No. 2, 1996, pp. 101-116) (Year: 1996).*

(Continued)

*Primary Examiner* — Amara Abdi
(74) *Attorney, Agent, or Firm* — Harness, Dickey & Pierce, P.L.C.

(57) ABSTRACT

A biological information measuring apparatus includes a cover member and a hardware processor. The cover member is provided with sensors for detecting biological signals to cover a position of a biological part of a subject. The hardware processor is configured to estimate a positional relation of the position of the biological part of the subject with respect to the cover member at a first time point. The hardware processor superimposes first point cloud and second point cloud. The first point cloud is acquired by a non-contact mechanism front the subject at the first time point and represents a surface of the biological part of the subject in a coordinate system of the sensors. The second point cloud is created based on a morphological image of the subject captured by a biological structure acquiring apparatus and represents the surface of the biological part of the subject.

19 Claims, 9 Drawing Sheets

(51) Int. Cl.
    *A61B 5/00*     (2006.01)
    *G06T 7/00*     (2017.01)
    *A61B 5/369*     (2021.01)

(52) U.S. Cl.
    CPC ............ *A61B 5/746* (2013.01); *G06T 7/0012* (2013.01); *G06T 2207/10028* (2013.01); *G06T 2207/30016* (2013.01)

(58) Field of Classification Search
    CPC ......... G06T 7/0012; G06T 2207/10028; G06T 2207/30016; G06T 7/74; G06T 2207/10004; G06T 2207/10088
    See application file for complete search history.

(56) References Cited

U.S. PATENT DOCUMENTS

| | | | | |
|---|---|---|---|---|
| 2013/0295016 | A1* | 11/2013 | Gerber | A61B 5/4833 424/9.2 |
| 2015/0338917 | A1* | 11/2015 | Steiner | H04L 9/3271 345/156 |
| 2016/0227193 | A1 | 8/2016 | Osterwood et al. | |
| 2017/0135655 | A1* | 5/2017 | Wang | G06T 11/008 |
| 2018/0088340 | A1* | 3/2018 | Amayeh | G02B 27/0172 |
| 2018/0333066 | A1* | 11/2018 | Yoo | A61B 5/316 |
| 2018/0343432 | A1* | 11/2018 | Duan | G01S 17/894 |
| 2019/0000389 | A1 | 1/2019 | Hikida | |
| 2019/0222330 | A1* | 7/2019 | Shan | H04B 1/707 |
| 2019/0282111 | A1* | 9/2019 | Yamagata | A61B 5/163 |
| 2022/0160445 | A1* | 5/2022 | Meglan | A61B 50/13 |

FOREIGN PATENT DOCUMENTS

| | | |
|---|---|---|
| JP | H10-143652 | 5/1998 |
| JP | 2002-500909 A | 1/2002 |
| JP | 2016-513804 A | 5/2016 |
| JP | 2019-13284 A | 1/2019 |
| JP | 2019-162410 | 9/2019 |
| WO | WO-2006/068103 A1 | 6/2006 |

OTHER PUBLICATIONS

Rasmus Zetter, et al., ("Optical Co-registration of MRI and On-scalp MEG", bioRxiv preprint first posted online Dec. 17, 12018; doi: http://dx.doi.org/10.1101/498113. (Year: 2018).*

JP Office Action dated Dec. 6, 2022 for corresponding Japanese Patent Application No. 2019-070167 with English machine translation.

D.Schwartz, D.Lemoine, E.Poiseau, and C.Barillot, "Registration of MEG/EEG Data with 3D MRI:Methodology and Precision Issues", Brain Topography, vol. 9, No. 2, 1996 pp. 101-116.

Rasmus Zetter, et al., Optical Co-registration of MRI and On-scalp MEG, bioRxiv preprint first posted online Dec. 17, 2018; doi: http://dx.doi.org/10.1101/498113.

U.S. Appl. No. 16/589,695 (dated Oct. 1, 2019).

* cited by examiner

BIOLOGICAL INFORMATION MEASURING APPARATUS, BIOLOGICAL INFORMATION MEASUREMENT METHOD, AND RECORDING MEDIUM

CROSS-REFERENCE TO RELATED APPLICATIONS

The present application claims priority under 35 U.S.C. § 119 to Japanese Patent Application No. 2019-070167, filed on Apr. 1, 2019. The contents of which are incorporated herein by reference in their entirety.

BACKGROUND OF THE INVENTION

1. Field of the Invention

The present invention relates to a biological information measuring apparatus, a biological information measurement method, and a recording medium.

2. Description of the Related Art

Traditionally, in the measurement of a biomagnetic field that reflects nervous activity, the alignment of a biological structure image such as a magnetic resonance (MR) image with the position of a biological part at the time of the magnetic field measurement is performed as preparation for analysis for the purpose of interrogating in which portion of the biological part a neural activity has occurred and interrogating when the neural activity has occurred.

For example, for a magnetoencephalograph for measuring a magneto-encephalography (MEG), marker coils are attached to a subject during magnetoencephalographic measurement and the head portion of the subject is aligned based on information of the positions of the marker coils (refer to D. Schwartz, D. Lemoine, E. Poiseau, and C. Barillot, "Registration of MEG/EEG Data with 3D MRI: Methodology and Precision Issues", Brain Topography, Volume 9, Number 2, 1996 pp. 101-116). In this head-position tracking method, however, magnetic fields caused by the marker coils prevent magnetic fields to be measured. In addition, it takes time, usually more than 20 minutes, to attach the marker coils and the correspondingly located vitamin E tablet or the like that can be captured within the MR image. Based on these cons for using marker coils, a technique for alignment without marker coils is requested.

Japanese Unexamined Patent Application Publication No. 04-109932 (hereinafter "Patent Literature 1") discloses a technique for detecting the position of a head without a marker coil for a magnetoencephalograph having a superconducting quantum interference device (SQUID) sensor. The SQUID sensor is fixed in a dewar. Specifically, the technique disclosed in the Patent Literature 1 is to detect relative position relations between the subject's head and the SQUID sensor by attaching reference marks to the subject's head and a dewar, capturing images of the head and the dewar, and processing the images.

The technique disclosed in the Patent Literature 1 can detect, without a marker coil, the position of the head of the subject in a sensor coordinate system of the magnetoencephalograph in real time. On the other hand, with regard to a method of aligning a morphological image (including an interior morphological image) of the head with the head of the subject, it is assumed to use a traditional method, such as a method using a marker coil or a method using a digitizer.

Therefore, a technique that is able to align a biological structure image with the position of a biological part without a marker coil and track the position of the biological part in real time is requested, which is necessary to analyze in which portion of a biological part a neural activity has occurred and analyze when the neural activity has occurred.

SUMMARY OF THE INVENTION

A biological information measuring apparatus includes: a cover member in which a plurality of sensors for detecting biological signals are disposed to cover a position of a biological part of a subject; a memory; and a hardware processor coupled to the memory and configured to estimate a positional relation of the position of the biological part of the subject with respect to the cover member at a first time point. The hardware processor superimposes first point cloud and second point cloud, the first point cloud being acquired in a non-contact manner from the subject at the first time point and representing a surface of the biological part of the subject in a coordinate system of the sensors, the second point cloud being created based on a morphological image of the subject captured by a biological structure acquiring apparatus and representing the surface of the biological part of the subject.

BRIEF DESCRIPTION OF THE DRAWINGS

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
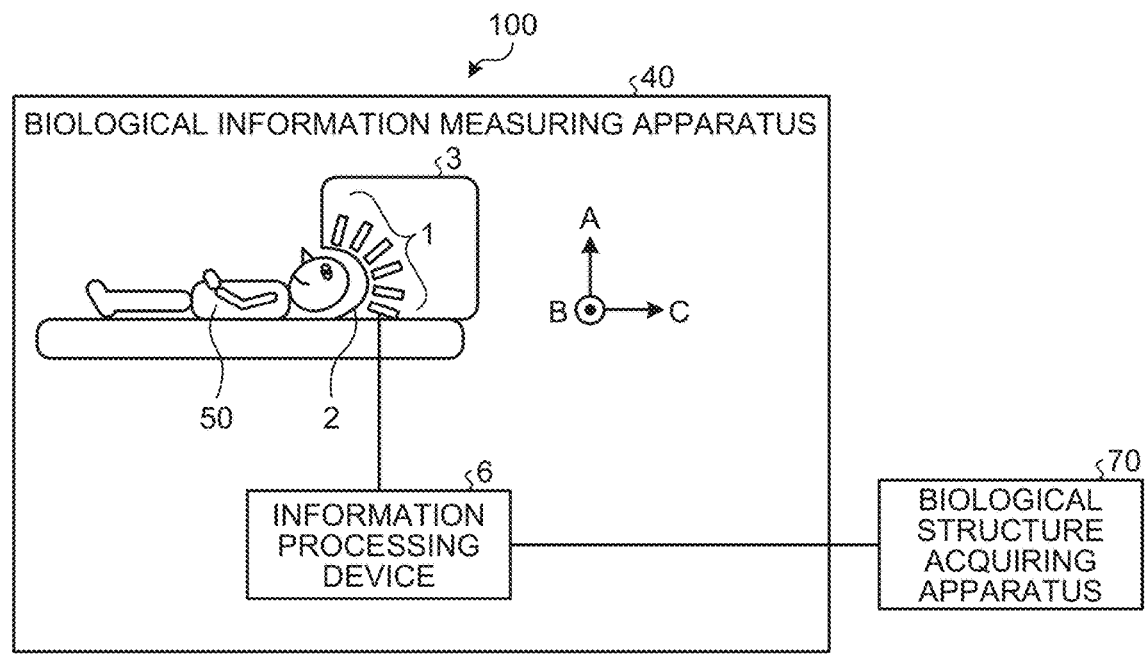
FIG. 1 is a diagram illustrating an example of a system configuration of a biological information measurement system according to a first embodiment.

The terminology used herein is for the purpose of describing particular embodiments only and is not intended to be limiting of the present invention.

As used herein, the singular forms "a", "an" and "the" are intended to include the plural forms as well, unless the context clearly represents otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

The present invention is directed to a need to align a biological structure image with the position of a biological part without a marker coil and to locate the position of the biological part in a sensor coordinate system at a desired time point.

Hereinafter, embodiments of a biological information measuring apparatus, a biological information measurement method, and a recording medium will be described in detail with reference to the accompanying drawings.

First Embodiment

FIG. 1 is a diagram illustrating an example of a system configuration of a biological information measurement system 100 according to a first embodiment. As illustrated in FIG. 1, the biological information measurement system 100 includes a biological information measuring apparatus 40 and a biological structure acquiring apparatus 70. The biological structure acquiring apparatus 70 is, for example, a magnetic resonance (MR) imaging apparatus for capturing an MR image. The biological structure acquiring apparatus 70 is not limited to the MR imaging apparatus and may be an X-ray computed tomography (CT) imaging apparatus or the like.

The biological information measuring apparatus 40 includes a magnetoencephalograph 3 and an information processing device 6.

The magnetoencephalograph 3 measures a magneto-encephalography (MEG) signal. A subject 50 to be measured puts the head into a dewar 2 of the magnetoencephalograph 3 in a state in which electrodes (or sensors) for electroencephalographic measurement are attached to the head of the subject 50 in magnetoencephalographic measurement of a biomagnetic field (brain magnetic field) that is biological information. When a brain wave is not measured at the same time, it is not necessary to attach the electrodes for electroencephalographic measurement to the head. The dewar 2 is a helmet-type sensor storage dewar that is a cover member for covering an almost entire region of the head of the subject 50. A plurality of magnetic sensors 1 for magnetoencephalographic measurement are installed in the dewar 2. When superconducting sensors (for example, superconducting quantum interference device (SQUID) sensors) that need to operate in an ultra-low temperature environment are used as the magnetic sensors 1, the dewar 2 also serves as a holding member in the ultra-low temperature environment in which liquid helium is used. The magnetoencephalograph 3 collects electroencephalographic signals from the electrodes and collects magnetoencephalographic signals from the magnetic sensors 1. The magnetoencephalograph 3 outputs the collected biological signals to the information processing device 6.

Although the dewar 2 including the magnetic sensors 1 are generally installed in a magnetic shield room, an illustration of the magnetic shield room is omitted for convenience.

As the magnetic sensors 1, which are needed to be able to measure a biomagnetism level lower than geomagnetism, SQUID sensors, tunnel magneto resistance (TMR) sensors, optically pumped atomic magnetometer (OPM) sensors, nitrogen-vacancy (NV) center sensors, or the like can be used. The magnetoencephalograph 3 includes the magnetic sensors 1 to locate a source of a biomagnetic field (brain magnetic field). Relative positions of the magnetic sensors 1 may be permanently fixed or appropriately changed for each time of measurement. The relative positions of the magnetic sensors 1 are in a certain determined arrangement at least within a measurement time period. Then, a sensor coordinate system is defined for the determined arrangement of the magnetic sensors 1. The sensor coordinate system is referred to as sensor coordinate system ABC for convenience of explanation.

Although a signal generated from brain neural activity of the subject 50 is detected by the magnetic sensors 1 in the biological information measurement system 100, the biological information measurement system 100 is not limited to measuring magnetic fields. It is sufficient if the sensors for detecting a signal generated from a neural activity of the brain in less invasive or preferably not invasive way are included in the biological information measurement system 100. Examples of the sensors that exclude the magnetic sensors are electroencephalographic sensors (potential sensors) and optical topographies (near-infrared sensors).

The magnetic sensors 1 according to the first embodiment may include a plurality of types of sensors among the foregoing sensors. In this case, however, it is desirable that an operation of one sensor do not affect measurement by the other sensors. Especially, in the case where a magnetic sensor is used as one of the sensors, even when a biological part is not directly in contact with the magnetic sensor, the magnetic sensor can acquire a signal emitted from the biological part and an attachment state of the sensor does not affect the measurement result. Therefore, the magnetic sensors 1 are suitable for the embodiment of the invention.

The information processing device 6 synchronizes and displays waveforms of magnetoencephalographic signals from the magnetic sensors 1 and waveforms of electroencephalographic signals from the electrodes on the same time axis. The electroencephalographic signals represent, as a potential difference between the electrodes, an electric activity (flow of ion charges that occurs in dendrites of neurons in synaptic transmission) of nerve cells. The magnetoencephalographic signals represent a minute magnetic field generated by an electric activity of the brain and a variation in the magnetic field.

In addition, the information processing device 6 receives a tomographic image (MR image) of the head of the subject 50, which is captured by the biological structure acquiring apparatus 70, The biological structure acquiring apparatus 70 may execute the image capturing before or after magnetic measurement by the magnetoencephalograph 3, and image data obtained is transmitted to the information processing device 6 online or offline. Detailed biomagnetic field analysis can be executed by using a morphological image of the inside of the biological part.

Figure 2:
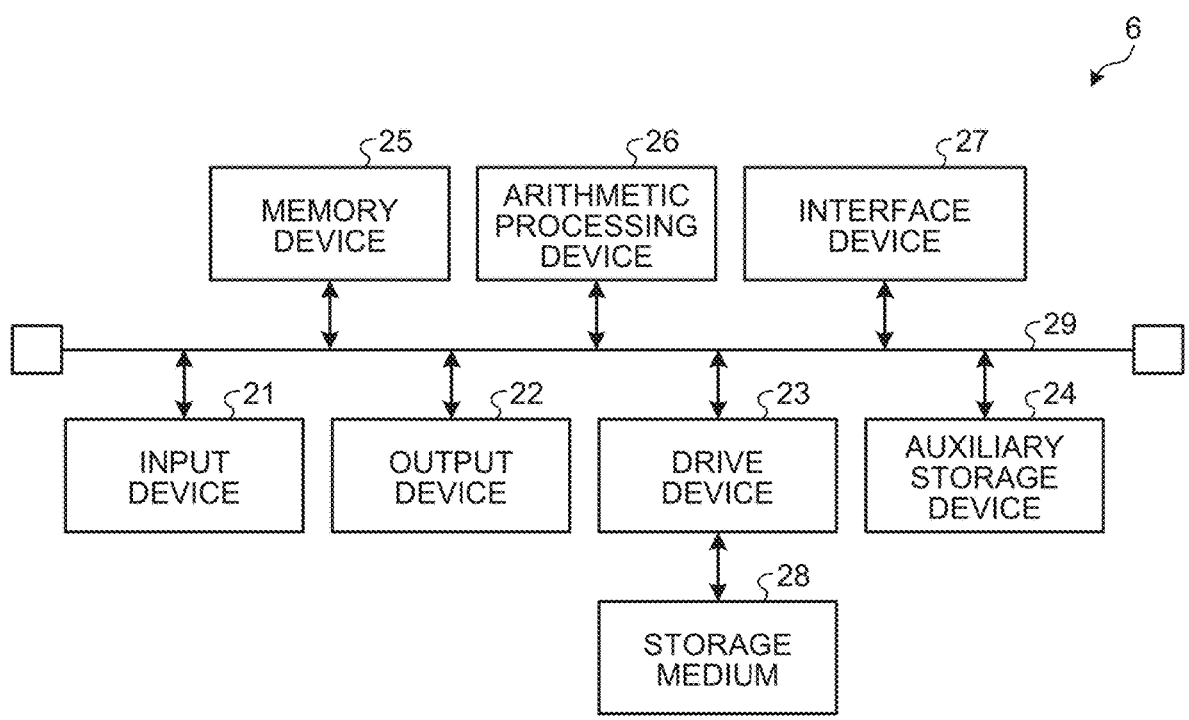
FIG. 2 is a diagram illustrating a hardware configuration of an information processing device.

The information processing device 6 will be further described below. FIG. 2 is a diagram illustrating an example of a hardware configuration of the information processing device 6.

The information processing device 6 includes an input device 21, an output device 22, a drive device 23, an auxiliary storage device 24, a memory device 25, an arithmetic processing device 26 (a hardware processor), and an interface device 27 that are connected to each other via a bus 29. The auxiliary storage device 24 stores a biological information measurement program.

The input device 21 inputs various information and is implemented by, for example, a keyboard, or a pointing device. The output device 22 outputs various information and is implemented by, for example, a display. The interface device 27 includes a LAN card and is used for connection to a network.

The biological information measurement program is at least part of various computer programs for controlling the information processing device 6. The biological information measurement program is provided by distributing a storage medium 28, or downloaded from the network, or the like. As the storage medium 28 storing the biological information measurement program, various types of storage media can be used. Such media include a storage medium that optically, electrically, or magnetically stores information such as a compact disc read only memory (CD-ROM), a flexible disk, and a magneto-optical disc, and a semiconductor memory that electrically stores information such as a ROM and a flash memory.

When the storage medium 28 storing the biological information measurement program is set in the drive device 23, the biological information measurement program is installed in the auxiliary storage device 24 from the storage medium 8 via the drive device 23. The biological information measurement program downloaded from the network is installed in the auxiliary storage device 24 via the interface device 27.

The auxiliary storage device 24 stores the installed biological information measurement program and stores necessary files, data, and the like. The memory device 25 reads and stores the biological information measurement program from the auxiliary storage device 24 upon the activation of the information processing device 6. The arithmetic processing device 26 implements various processes described later in accordance with the biological information measurement program stored in the memory device 25.

The information processing device 6 according to the present embodiment correctly measures positional relations between the brain of the subject 50 and the magnetic sensors 1.

Figure 3:
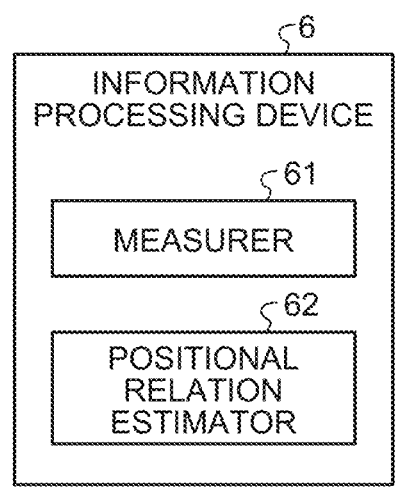
FIG. 3 is a diagram describing functions of the information processing device.

Next, characteristic functions among functions of the information processing device 6 according to the present embodiment will be described. FIG. 3 is a diagram describing the functions of the information processing device 6.

The information processing device 6 includes a measurer 61 and a positional relation estimator 62 that is a positional relation estimating section.

The measurer 61 and the positional relation estimator 62 are implemented by that the arithmetic processing device 26 (hardware processor) reads and executes the biological information measurement program stored in the auxiliary storage device 24, the memory device 25, or the like.

The measurer 61 measures a brain neural activity based on biological signals (magnetoencephalographic signals) detected by the magnetic sensors 1 in response to a stimulus.

The positional relation estimator 62 estimates a positional relation of the position of the biological part (head) of the subject with respect to the dewar 2 (magnetic sensors 1) at a first time point. Specifically, the positional relation estimator 62 superimposes first point cloud and second point cloud, the first point cloud being acquired by a non-contact mechanism front the subject at the first time point and representing a surface of the biological part of the subject in the sensor coordinate system ABC of the magnetic sensors 1, the second point cloud being created based on a morphological image of the subject captured by the biological structure acquiring apparatus 70 and representing the surface of the biological part of the subject.

Figure 4:
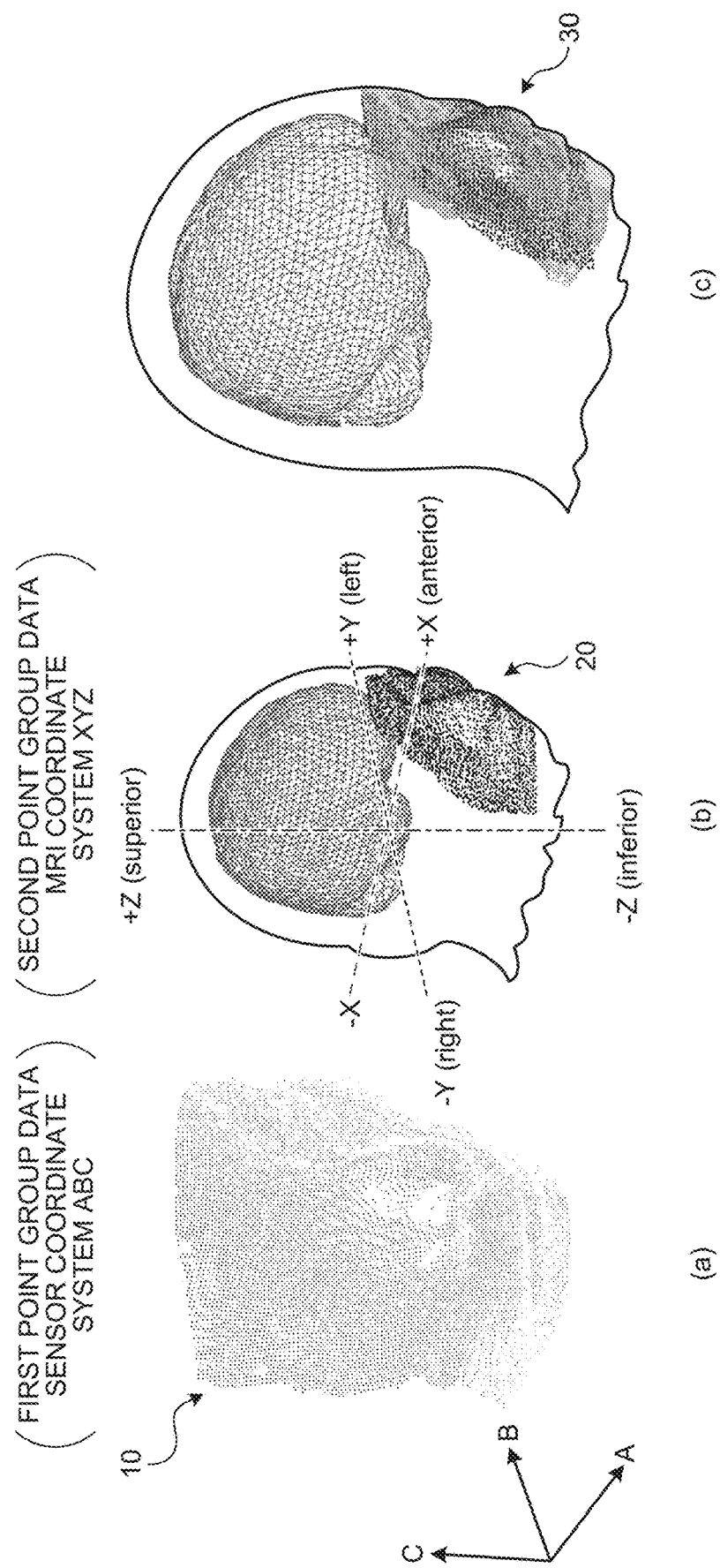
FIG. 4 is a diagram illustrating an example of superimposition of first point cloud and second point cloud.

FIG. 4 is a diagram illustrating an example of the superimposition of the first point point cloud and the second point point cloud. In FIG. 4, data (a) represents first point cloud 10, and data (b) represents second point cloud 20. A reference sign 30 illustrated in data (c) represents the superimposed first and second point point cloud 10 and 20, showing that the two point clouds are at the almost same position. Especially each nose part on the two face point clouds are matched well. The second point cloud 20 representing the surface of the biological part of the subject 50 is represented in a biological structure coordinate system XYZ.

As illustrated in FIG. 4, the positional relation estimator 62 of the information processing device 6 obtains the superimposed data 30 by executing a process of superimposing the first point cloud 10 and the second point point cloud 20. The first point cloud 10 represents the surface of the biological part of the subject 50 in the sensor coordinate system ABC. The second point point cloud 20 is created based on the morphological image of the subject 50 captured by the biological structure acquiring apparatus 70 and represents the surface of the biological part of the subject 50. The biological structure acquiring apparatus 70 may be an MR imaging apparatus or an X-ray CT imaging apparatus. By obtaining the superimposed data 30, the positional relation estimator 62 of the information processing device 6 estimates a positional relation of the position of the biological part (head) of the subject 50 in the sensor coordinate system with respect to the dewar 2 (magnetic sensors 1) at a desired time point during the measurement. The positional relation can be represented as a transformation matrix composed of six degrees of freedom (translation and rotation).

By executing the superimposition process described above, a transformation matrix between the biological structure coordinate system XYZ and the sensor coordinate system ABC can be obtained, and the location where the biological part (for example, the head or the brain as the inner structure of the head) of the subject 50 in the biological structure coordinate system XYZ exists in the sensor coordinate system ABC is located. That time (the first time point) indicates an acquisition time when data as a base of the first point cloud 10 is acquired. By setting the acquisition time within the measurement time period, the position of the biological part of the subject 50 in the sensor coordinate system ABC at a desired time point during the measurement is located.

The second point cloud 20 can be obtained as mesh data of vertices of surface (for example, facial) of the subject 50, which is extracted from structural data of the subject 50 by using existing software. The superimposition process can be executed by using, for example, the iterative closest point (ICP) algorithm.

In the present embodiment, an external nose portion is included in the first point cloud 10 and the second point cloud 20. The superimposing point clouds can be accurately executed using point cloud of the large convexity. The degree of convexity of the external nose portion is large on the facial surface, allowing us to utilize such an accurate superimposition. Especially, the accuracy can be improved when the ICP algorithm is used.

According to the present embodiment described above, a biological structure image and the position of the biological part can be aligned with each other without a marker coil, and the position of the biological part in the sensor coordinate system ABC can be located at a desired time point.

Second Embodiment

Next, a second embodiment will be described. The second embodiment is different from the first embodiment in that the first point cloud 10 is acquired by a depth imaging device. In the description of the second embodiment, the description of the same features as those described in the first embodiment is omitted. Different features from the first embodiment will be described in the second embodiment.

Figure 5:
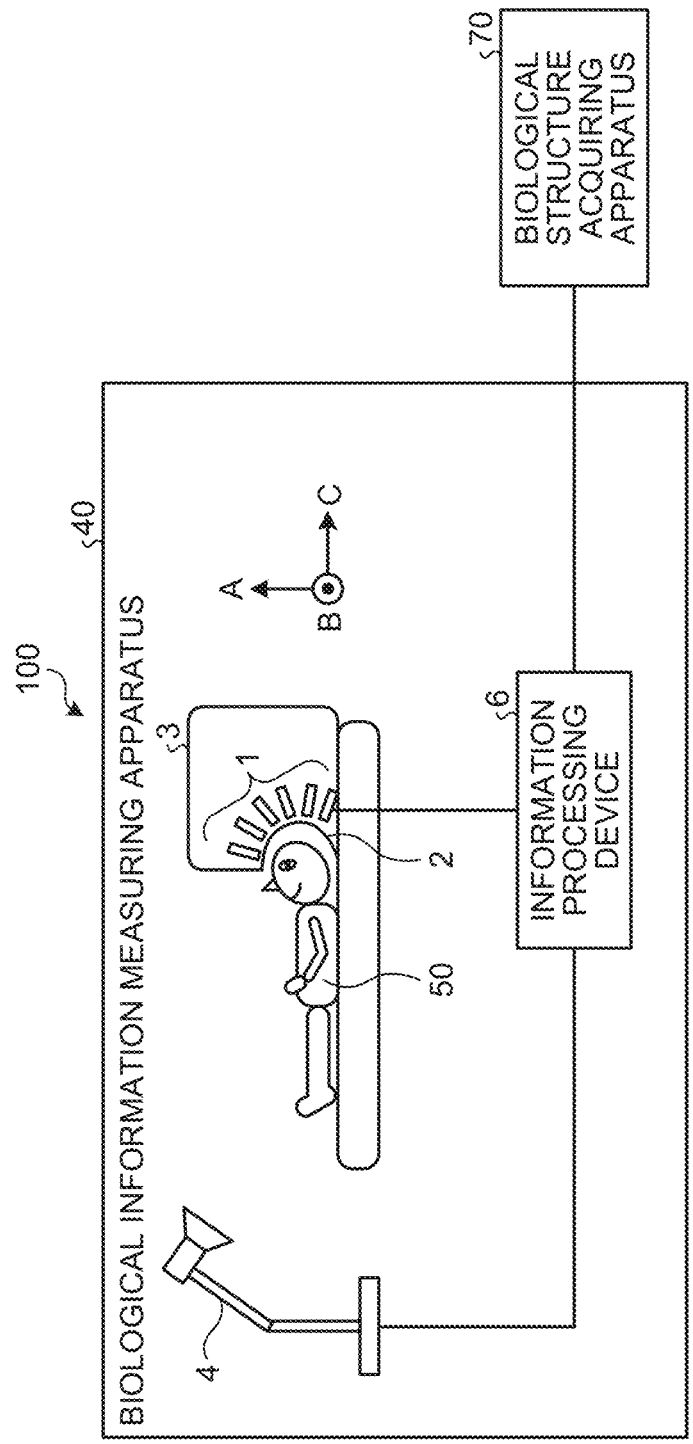
FIG. 5 is a diagram illustrating an example of a system configuration of a biological information measurement system according to a second embodiment.

FIG. 5 is a diagram illustrating an example of a system configuration of a biological information measurement system 100 according to the second embodiment. As illustrated in FIG. 5, the biological information measurement system 100 includes a depth imaging device 4 installed at a predetermined position. The depth imaging device 4 is connected to the information processing device 6 via the interface device 27. The positional relation estimator 62 of the information processing device 6 of the biological information measurement system 100 acquires, by using the depth imaging device 4, the first point cloud 10 in a non-contact manner with the subject 50.

As the depth imaging device 4, a stereo camera, such as Kinect (registered trademark) of Microsoft (registered trademark) Corporation or RealSense (registered trademark) of Intel (registered trademark) Corporation, can be used. In addition, as the depth imaging device 4, not only such stereo cameras but also LiDAR, a galvanometer scanner, or the like can be used.

The depth imaging device 4 is installed at the predetermined position and can represent the first point cloud 10 in the sensor coordinate system ABC. It is, therefore, necessary to execute in advance calibration for matching a coordinate system the depth imaging device 4 has with the sensor coordinate system ABC.

Three examples of the calibration method for matching the coordinate system of the depth imaging device 4 with the sensor coordinate system ABC will be described below.

Method 1: Representing Point cloud by Depth Imaging Device 4 in Sensor Coordinate System ABC A biological phantom is prepared, and a plurality of (at least three) marker coils is attached to a surface of the biological phantom. The biological phantom is arranged and fixed in a space in which magnetic fields of the marker coils can be measured by the magnetic sensors 1. The marker coils are operated. Then, the magnetic fields of the marker coils are measured by the magnetic sensors 1, and, at the same time, the biological phantom is imaged by the depth imaging device 4. At this time, it is necessary for the marker coils to be included in a depth image obtained by the depth imaging device 4. By estimating the positions of the marker coils based on the marker coils' magnetic fields measured by the magnetic sensors 1, the positions of the marker coils in the sensor coordinate system ABC are located.

On the other hand, the positions of the corresponding marker coils in the coordinate system specific to the depth imaging device 4 are identified from the depth image. The transformation matrix between the coordinate system specific to the depth imaging device 4 and the sensor coordinate system ABC can be obtained from the multiple marker coil positions of the two groups. Therefore, the point cloud acquired by the depth imaging device 4 can be represented in the sensor coordinate system ABC. Although the biological part may be used instead of the biological phantom, the biological part moves and has a sagging part. Thus, the phantom is preferable to use.

Method 2: Representing Point cloud by Depth Imaging Device 4 in Sensor Coordinate System ABC The biological phantom and 3D surface-shaped data thereof are prepared. As the surface-shaped data, 3D-CAD data for phantom generation can be used. Alternatively, when the biological phantom can be imaged by an MR imaging apparatus and MR image capturing is executed, the surface-shaped data is calculated by using existing software. The surface-shaped data is normally mesh data. Similar to the foregoing first method, a plurality of (at least three) marker coils are attached to a surface of the biological phantom. Mesh data of the biological phantom, which is arranged at a predetermined position and oriented in a predetermined direction, is represented in the sensor coordinate system ABC by operating the marker coils.

On the other hand, the depth imaging device 4 acquires depth point cloud of the biological phantom arranged at the predetermined position and oriented in the predetermined direction. By using the ICP or the like to superimpose the foregoing mesh data and the point cloud, the point cloud acquired by the depth imaging device 4 can be represented in the sensor coordinate system ABC.

Method 3: Representing Point Cloud by Depth Imaging Device 4 in Sensor Coordinate System ABC 3D-CAD data of a body of the magnetoencephalograph 3 constituting the biological information measuring apparatus 40 is prepared. A body (for example, the dewar 2 of the magnetoencephalograph 3) is imaged by the depth imaging device 4. By using the ICP or the like to superimpose imaging data and the 3D-CAD data of the body structure, the point cloud acquired by the depth imaging device 4 can be represented in the sensor coordinate system ABC.

The biological information measuring apparatus 40 according to the embodiment is configured to execute, as a signal processing algorithm for measurement data, a signal processing algorithm that uses a projector to a spatial-domain signal subspace and a time-domain signal subspace for a measurement signal. This algorithm is referred to as DSSP (Dual signal subspace projection, for details, see Kensuke Sekihara, Yuya Kawabata, Shuta Ushio, Satoshi Sumiya, Shigenori Kawabata, Yoshiaki Adachi and Srikantan S Nagarajan4 Journal of Neural Engineering, Volume 13, Number 3 (2016).)algorithm. Electromagnetic noise caused by the depth imaging device 4 and included in the measurement data can be removed by the DSSP algorithm.

Figure 6:
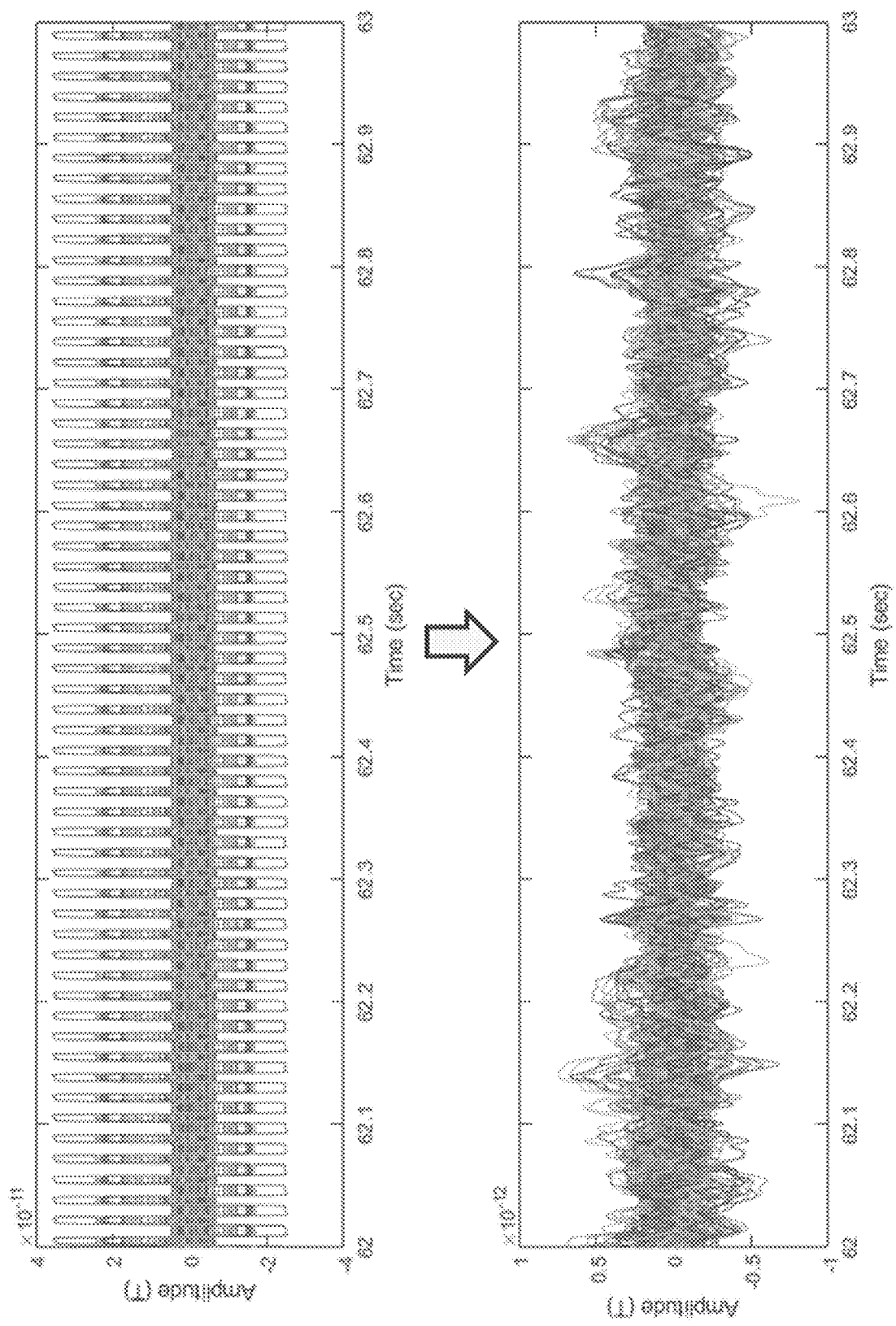
FIG. 6 is a diagram illustrating an example of measurement data (upper panel) and the cleaned data (lower panel) that is obtained by applying DSSP algorithm to the measurement data for removal of electromagnetic noise.

FIG. 6 is a diagram illustrating an example of the measurement data (upper panel) and the data (lower panel) that is obtained by applying the DSSP to the measurement data for the removal of the electromagnetic noise. As an example, the illustration shows 160 pieces of SQUID sensor time-series data for a time period from a time point of 62 seconds to a time point of 63 seconds in measurement. As illustrated in FIG. 6, during the magnetoencephalographic measurement, periodical electromagnetic noise of approximately 10 pT caused by the depth imaging device 4 is clearly removed by the biological information measuring apparatus 40, and only magnetic field data of less than 1 pT remains. By installing the DSSP algorithm in the information processing device 6, the electromagnetic noise caused by the depth imaging device 4 can be removed in real time.

According to the present embodiment, as described above, a biological structure image and the position of the biological part can be aligned with each other without a marker coil, and the position of the biological part in the sensor coordinate system ABC can be located at a desired time point.

Third Embodiment

Next, a third embodiment will be described. The third embodiment is different from the foregoing first and second embodiments in that, the first point cloud 10 is acquired by a two-dimensional pixel image capturing device. In the third embodiment, the description of the same features as those described in the first and the second embodiments is omitted. Different features from the first and the second embodiments will be described in the third embodiment.

Figure 7:
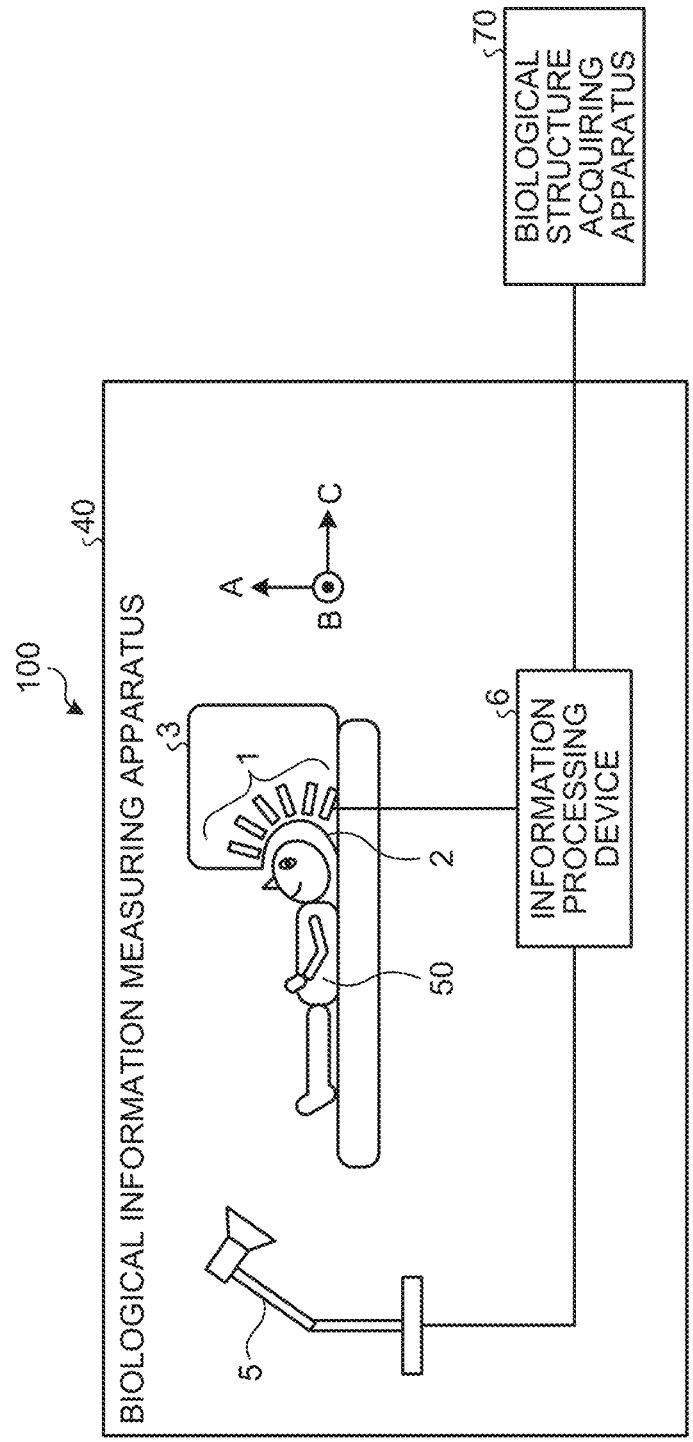
FIG. 7 is a diagram illustrating an example of a system configuration of a biological information measurement system according to a third embodiment.

FIG. 7 is a diagram illustrating an example of a system configuration of a biological information measurement system 100 according to the third embodiment. As illustrated in FIG. 7, the biological information measurement system 100 includes a two-dimensional pixel image capturing device 5 that is an image capturing device installed at a predetermined position. The two-dimensional pixel image capturing device 5 is connected to the information processing device 6 via the interface device 27.

The positional relation estimator 62 of the information processing device 6 of the biological information measurement system 100 acquires the first point cloud 10 in a non-contact manner with the subject 50 by using a two-dimensional image captured by the two-dimensional pixel image capturing device 5. Specifically, the first point cloud 10 is acquired by estimating depth information of the subject from the captured two-dimensional pixel image.

For example, the depth information of the subject can be accurately estimated from the two-dimensional pixel image by utilizing deep-learning techniques, specifically executing learning process for a convolutional neural network (ConvNet; CNN) or a generative adversarial network (GAN) using a set of many depth images and the two-dimensional pixel image. It is preferable that the images for the learning are captured to include the biological part and the body of the magnetoencephalograph 3 constituting the biological information measuring apparatus 40.

In the case of the magnetoencephalograph 3, the two-dimensional pixel image capturing device 5 may be used to image the face of the subject 50 and estimate depth information of some feature points on the subject face from the captured two-dimensional pixel image. For example, existing software or Open Face [https://github.com/TadasBaltrusaitis/OpenFace] can be used for the estimation.

According to the present embodiment, as described above, a biological structure image and the position of the biological part can be aligned with each other without a marker coil, and the position of the biological part in the sensor coordinate system ABC can be located at a desired time point.

Fourth Embodiment

Next, a fourth embodiment will be described. The fourth embodiment is different from the first to the third embodiments in that, the depth imaging device 4 and the two-dimensional pixel image capturing device 5 are used. In the fourth embodiment, the description of the same features as those described in the first to the third embodiments is omitted. Different features from the first to the third embodiments will be described in the fourth embodiment.

Figure 8:
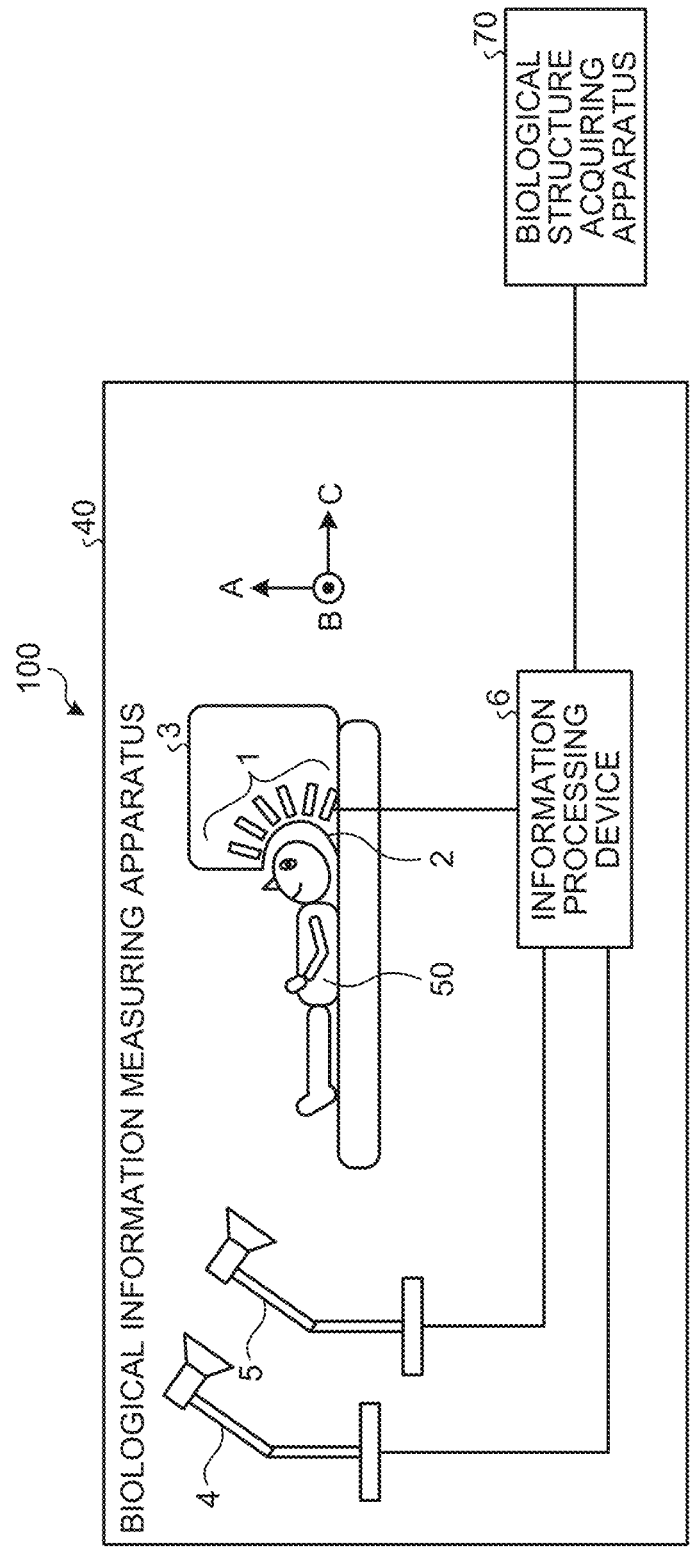
FIG. 8 is a diagram illustrating an example of a system configuration of a biological information measurement system according to a fourth embodiment.

FIG. 8 is a diagram illustrating an example of a system configuration of a biological information measurement system 100 according to the fourth embodiment. As illustrated in FIG. 8, the biological information measurement system 100 includes the depth imaging device 4 installed at a predetermined position and the two-dimensional pixel image capturing device 5 installed at a predetermined position. The depth imaging device 4 and the two-dimensional pixel image capturing device 5 are connected to the information processing device 6 via the interface device 27.

The depth imaging device 4 is an active imaging device that emits infrared laser or the like. The two-dimensional pixel image capturing device 5 is a passive imaging device such as a CCD camera.

At a first time point during magnetoencephalographic measurement, the positional relation estimator 62 of the information processing device 6 in the biological information measurement system 100 acquires, by using the depth imaging device 4, the first point cloud 10 in a non-contact manner with the subject 50, and acquires, by using the two-dimensional pixel image capturing device 5, a first two-dimensional pixel image in a non-contact manner with the subject 50. Further, at a second time point during the magnetoencephalographic measurement, the positional relation estimator 62 acquires, by using the two-dimensional pixel image capturing device 5, a second two-dimensional pixel image in a non-contact manner with the subject 50.

The positional relation estimator 62 of the information processing device 6 instructs the two-dimensional pixel image capturing device 5 to operate with a frequency of 1 Hz or higher in the magnetoencephalographic measurement. As the positional relation estimator 62 instructs the two-dimensional pixel image capturing device 5 to operate with the frequency of 1 Hz or higher, a movement of the biological part of the subject 50 can be monitored with a sampling frequency of 1 Hz or higher.

In addition, the positional relation estimator 62 of the information processing device 6 instructs the depth imaging device 4 to operate with a frequency of 1 Hz or higher and acquires the first point cloud 10 with a sampling frequency of 1 Hz or higher. Therefore, a movement of the biological part of the subject 50 can be monitored with the sampling frequency of 1 Hz or higher.

Then, based on the first two-dimensional pixel image and the second two-dimensional pixel image, the positional relation estimator 62 of the information processing device 6 estimates a positional relation of the position of the biological part (head portion) of the subject 50 with respect to the dewar 2 (magnetic sensors 1) at the second time point.

In the present embodiment, at a first time point, the first point cloud 10 is acquired by using the depth imaging device 4. By this, the position of the biological part of the subject is identified, which is included in the first two-dimensional pixel image at the first time point in the sensor coordinate system ABC. In addition, relative misalignment (rotation and translation) of the biological part of the subject 50 is determined front the first two-dimensional pixel image at the first time point and the second two-dimensional pixel image at the second time point. Thus, it is possible to locate the position of the biological part of the subject 50 at the second time point without operating the depth imaging device 4.

In general, an active imaging device emits electromagnetic noise larger than that of a passive imaging device. The electromagnetic noise becomes noise against the magnetoencephalographic measurement by the magnetic sensors 1. In the present embodiment, the depth imaging device 4 being an active imaging device is operated only at the first time point. It is therefore possible to avoid the electromagnetic noise caused by an operation of the depth imaging device 4 on measurement data during the measurement excluding the first time point.

In a case where the biological part is the head portion, a head-pose estimation method can be used to determine the relative misalignment (rotation and translation) of the biological part of the subject on the first two-dimensional pixel image at the first time point and the second two-dimensional pixel image at the second time point. Even for another biological part that is, for example, a body, the similar method, a body-pose estimation method, can be used.

According to the present embodiment, as described above, a biological structure image and the position of the biological part can be aligned with each other without a marker coil, and the position of the biological part in the sensor coordinate system ABC can be located at a desired time point.

Figure 9:
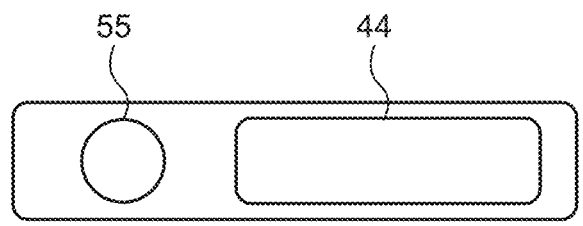
FIG. 9 is a diagram illustrating an example of a device obtained by unifying a depth imaging device and a two-dimensional pixel imaging device.

In FIG. 8, the depth imaging device 4 and the two-dimensional pixel image capturing device 5 are depicted separately. However, the depth imaging device 4 and the two-dimensional pixel image capturing device 5 may be unified. Specifically, as illustrated in FIG. 9, a depth imaging device section 44 that performs the functions of the depth imaging device 4 and a two-dimensional pixel image capturing device section 55 that performs the functions of the two-dimensional pixel image capturing device 5 may be unified and included in the same casing. When the unified imaging device is used, a space for the biological information measuring apparatus 40 can be saved.

Fifth Embodiment

Next, a fifth embodiment will be described. The fifth embodiment is different from the first to the fourth embodiments in that, the depth imaging device 4 is used to acquire the first point cloud 10 at a start time of magnetoencephalographic measurement, and after that, the position of the biological part (head) of the subject 50 is located from only a relative positional relation of the subject in a two-dimensional pixel image. In the description of the fifth embodiment, the description of the same features as those described in the first to the fourth embodiments is omitted. Different features from the first to the fourth embodiments will be described in the fifth embodiment.

Figure 10:
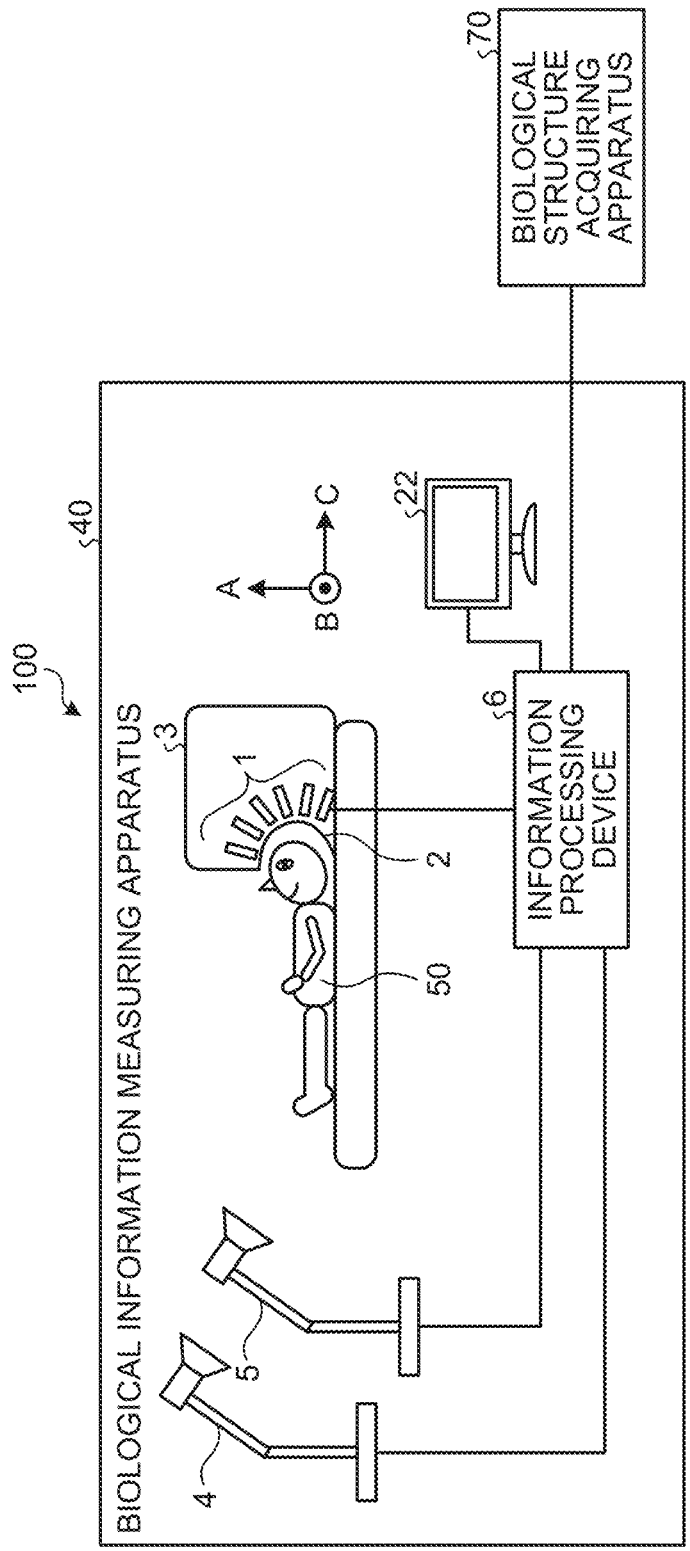
FIG. 10 is a diagram illustrating an example of a system configuration of a biological information measurement system according to a fifth embodiment.

FIG. 10 is a diagram illustrating an example of a system configuration of a biological information measurement system 100 according to the fifth embodiment. As illustrated in FIG. 10, the biological information measurement system 100 includes the depth imaging device 4 installed at a predetermined position and the two-dimensional pixel image capturing device 5 installed at a predetermined position. The depth imaging device 4 and the two-dimensional pixel image capturing device 5 are connected to the information processing device 6 via the interface device 27.

The depth imaging device 4 is an active imaging device that emits infrared laser or the like. The two-dimensional pixel image capturing device 5 is a passive imaging device such as a CCD camera.

At the start time of the magnetoencephalographic measurement, the information processing device 6 of the biological information measurement system 100 acquires the first point cloud 10 by using the depth imaging device 4 and acquires a first two-dimensional pixel image by using the two-dimensional pixel image capturing device 5. Further, at a time after the start of the magnetoencephalographic measurement, the information processing device 6 acquires a second two-dimensional pixel image by using the two-dimensional pixel image capturing device 5.

Then, the positional relation estimator 62 of the information processing device 6 in the biological information measurement system 100 estimates a positional relation of the position of the biological part (head portion) of the subject 50 with respect to the dewar 2 (magnetic sensors 1) at the second time point, based on the first two-dimensional pixel image and the second two-dimensional pixel image.

In the present embodiment, the positional relation estimator 62 acquires the first point cloud 10 by using the depth imaging device 4 at the start time of the magnetoencephalographic measurement, and locates the position of the biological part (head) of the subject 50 from only the relative positional relation of the subject within the two-dimensional pixel image.

Therefore, the position of the biological part of the subject 50 can be located at a desired time point (second time point) during the magnetoencephalographic measurement in real time. By tracking the position of the biological part, a movement of the subject 50 can be recognized in the magnetoencephalographic measurement, and it is possible to determine whether noise of measurement data has been caused by the movement of the subject 50.

A measurer sets a misalignment threshold for the misalignment of the position of the biological part at the start time of the magnetoencephalographic measurement in the positional relation estimator 62 of the information processing device 6, and the positional relation estimator 62 applies the threshold to biological part's position tracking data based on the first point cloud 10 and the second point cloud 20. When the position of the biological part is largely different from the threshold, the positional relation estimator 62 causes the output device 22 to display (or issue) an alert representing the difference in the magnetoencephalographic measurement.

Therefore, the measurer can determine whether to suspend and restart the magnetoencephalographic measurement or continue to perform the magnetoencephalographic measurement or the like. For the magnetoencephalograph 3, it is preferable to set the threshold to approximately 5 mm.

According to the present embodiment, as described above, a biological structure image and the position of the biological part can be aligned with each other without a marker coil, and the position of the biological part in the sensor coordinate system ABC can be located at a desired time point.

Although the foregoing embodiments describe the cases where the head portion is an example of the biological part, the biological part is not limited to this. For example, the biological part may be the cervical spine to be measured by a magnetospinography (MSG), and biological tracking in the MSG is included in the scope of the invention.

According to the present invention, it is possible to obtain an advantage that a biological structure image and the position of a biological part can be aligned with each other without a marker coil and the position of the biological part in a sensor coordinate system can be located in real time.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. A biological information measuring apparatus comprising:
    a cover member configured to cover a position of a biological part of a subject, the cover member including a plurality of sensors configured to detect biological signals from the biological part of the subject; and
    processing circuitry configured to estimate a positional relation of the position of the biological part of the subject with respect to the cover member at a first time point,
    wherein the estimating the positional relation includes,
        estimating the positional relation of the position of the biological part of the subject with respect to the cover member at the first time point with respect to six degrees of freedom, and
        superimposing a first point cloud and a second point cloud,
            the first point cloud being acquired by a non-contact mechanism from the subject at the first time point, the first point cloud representing a surface of the biological part of the subject in a coordinate system of the sensors, and
            the second point cloud being created based on a morphological image of the subject captured by a biological structure acquiring apparatus, the second point cloud representing the surface of the biological part of the subject.

2. The biological information measuring apparatus according to claim 1, wherein the processing circuitry is further configured to use as the first point cloud, depths measured by a depth imaging device installed at a desired position.

3. The biological information measuring apparatus according to claim 1, wherein the processing circuitry is further configured to use, as the first point cloud, a two-dimensional pixel image captured by an image capturing device installed at a desired position.

4. The biological information measuring apparatus according to claim 1, wherein the processing circuitry is further configured to:
    use the first time point as a time point during biological information measurement;
    use, as the first point cloud, depths measured by a depth imaging device installed at a first desired position;
    acquire a first two-dimensional pixel image captured by an image capturing device installed at a second desired position;
    acquire a second two-dimensional pixel image from the image capturing device at a second time point during the biological information measurement; and
    estimate, based on the first two-dimensional pixel image and the second two-dimensional pixel image, a positional relation of the position of the biological part of the subject with respect to the cover member at the second time point.

5. The biological information measuring apparatus according to claim 4, wherein the processing circuitry is further configured to use the first time point as a start time of the biological information measurement.

6. The biological information measuring apparatus according to claim 4, wherein the processing circuitry is further configured to set the second time point with a frequency of 1 Hz or higher.

7. The biological information measuring apparatus according to claim 2, wherein the processing circuitry is further configured to use, as the first point cloud, depths measured by the depth imaging device with a frequency of 1 Hz or higher.

8. The biological information measuring apparatus according to claim 3, wherein the processing circuitry is further configured to use, as the first point cloud, a two-dimensional pixel image captured by the image capturing device with a frequency of 1 Hz or higher.

9. The biological information measuring apparatus according to claim 2, wherein the depth imaging device is a stereo camera, LiDAR, or a galvanometer scanner.

10. The biological information measuring apparatus according to claim 1, wherein, in response to the position of the biological part of the subject exceeding a desired threshold with respect to the position of the biological part at a start time of biological information measurement, the processing circuitry is further configured to issue, during the biological information measurement, an alert representing that the position of the biological part exceeds the desired threshold.

11. The biological information measuring apparatus according to claim 1, wherein
    the cover member is configured to cover a head portion of the subject; and
    the first point cloud and the second point cloud each include an external nose portion of the subject.

12. The biological information measuring apparatus according to claim 2, wherein the processing circuitry is further configured to execute a signal processing algorithm using a projector to a spatial-domain signal subspace and a time-domain signal subspace for a measurement signal.

13. The biological information measuring apparatus according to claim 1, wherein the biological structure acquiring apparatus is a magnetic resonance imaging (MRI) apparatus or an X-ray computed tomography (CT) imaging apparatus.

14. A biological information measurement method implemented by a computer, the method comprising:
estimating a positional relation of a position of a biological part of a subject at a first time point with respect to a cover member which covers the position of the biological part of the subject, the cover member including a plurality of sensors which detect biological signals from the biological part of the subject, the estimating the positional relation including,
estimating the positional relation of the position of the biological part of the subject with respect to the cover member at the first time point with respect to six degrees of freedom, and
superimposing a first point cloud and a second point cloud, the first point cloud being acquired by a non-contact mechanism from the subject at the first time point,
the first point cloud representing a surface of the biological part of the subject in a coordinate system of the sensors, and
the second point cloud being created based on a morphological image of the subject captured by a biological structure acquiring apparatus, the second point cloud representing the surface of the biological part of the subject.

15. A non-transitory computer-readable recording medium on which computer readable instructions are recorded, which when executed by processing circuitry, cause the processing circuitry to:
estimate a positional relation of a position of a biological part of a subject at a first time point with respect to a cover member which covers the position of the biological part of the subject, the cover member including a plurality of sensors configured to detect biological signals from the biological part of the subject, the estimating the positional relation including,
estimating the positional relation of the position of the biological part of the subject with respect to the cover member at the first time point with respect to six degrees of freedom, and
superimposing a first point cloud and a second point cloud,
the first point cloud being acquired by a non-contact mechanism from the subject at the first time point, the first point cloud representing a surface of the biological part of the subject in a coordinate system of the sensors, and
the second point cloud being created based on a morphological image of the subject captured by a biological structure acquiring apparatus, the second point cloud representing the surface of the biological part of the subject.

16. The biological information measuring apparatus according to claim 1, wherein
the second point cloud represents the surface of the biological part of the subject in a coordinate system of the biological structure acquiring apparatus, the coordinate system of the biological structure acquiring apparatus being different than the coordinate system of the sensors.

17. The biological information measuring apparatus according to claim 1, wherein
the first point cloud represents an external surface of the biological part of the subject; and
the second point cloud represents an internal surface of the biological part of the subject.

18. The biological information measuring apparatus according to claim 1, wherein the processing circuitry is further configured to:
create the second point cloud without the use of markers placed on the surface of the biological part of the subject.

19. The biological information measuring apparatus according to claim 1, wherein the processing circuitry is further configured to:
superimpose the first point cloud and the second point cloud using an iterative closest point algorithm.

* * * * *